US008394807B2

(12) United States Patent
Ghosh

(10) Patent No.: US 8,394,807 B2
(45) Date of Patent: Mar. 12, 2013

(54) QUINAZOLINE INHIBITORS OF BACE 1 AND METHODS OF USING

(75) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 41 days.

(21) Appl. No.: 13/130,508

(22) PCT Filed: Nov. 20, 2009

(86) PCT No.: PCT/US2009/065358
§ 371 (c)(1),
(2), (4) Date: May 20, 2011

(87) PCT Pub. No.: WO2010/059953
PCT Pub. Date: May 27, 2010

(65) Prior Publication Data
US 2011/0230505 A1 Sep. 22, 2011

Related U.S. Application Data

(60) Provisional application No. 61/116,438, filed on Nov. 20, 2008, provisional application No. 61/175,630, filed on May 5, 2009.

(51) Int. Cl.
*A01N 43/54* (2006.01)
*A61K 31/517* (2006.01)
*C07D 401/00* (2006.01)
*C07D 403/00* (2006.01)
*C07D 413/00* (2006.01)
*C07D 417/00* (2006.01)
*C07D 419/00* (2006.01)
*C07D 239/72* (2006.01)

(52) U.S. Cl. ........................ 514/266.2; 544/284; 544/292
(58) Field of Classification Search ........................ None
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,630,200 | A | 12/1971 | Higuchi |
| 3,847,770 | A | 11/1974 | Radlowe et al. |
| 3,916,899 | A | 11/1975 | Theeuwes et al. |
| 4,008,719 | A | 2/1977 | Theeuwes et al. |
| 4,687,610 | A | 8/1987 | Vassilatos |
| 4,769,027 | A | 9/1988 | Baker et al. |
| 5,059,595 | A | 10/1991 | Grazie |
| 5,073,543 | A | 12/1991 | Marshall et al. |
| 5,120,548 | A | 6/1992 | McClelland et al. |
| 5,354,566 | A | 10/1994 | Addesso et al. |
| 5,591,767 | A | 1/1997 | Mohr et al. |
| 5,627,165 | A | 5/1997 | Glazier |
| 5,639,476 | A | 6/1997 | Oshlack et al. |
| 5,674,533 | A | 10/1997 | Santus et al. |
| 5,733,566 | A | 3/1998 | Lewis |
| 7,291,620 | B2 | 11/2007 | Coburn et al. |
| 7,348,356 | B2 | 3/2008 | Coburn et al. |
| 2006/0178383 | A1 | 8/2006 | Bischoff et al. |
| 2006/0229309 | A1 | 10/2006 | Thompson et al. |
| 2007/0213316 | A1 | 9/2007 | John et al. |
| 2007/0213331 | A1 | 9/2007 | Dally et al. |
| 2007/0259898 | A1 | 11/2007 | Baxter et al. |

FOREIGN PATENT DOCUMENTS

| WO | WO 2006/103038 | 10/2006 |
| WO | WO2007/058583 | 5/2007 |

OTHER PUBLICATIONS

A. K. Ghosh, et al., "Design of Potent Inhibitors for Human Brain Memapsin 2 (β-Secretase)," J. Am. Chem. Soc., 122:3522-3523 (2000).
L. Hong, et al., "Structure of the Protease Domain of Memapsin 2 (β-Secretase) Complexed with Inhibitor," Science, 290:150-153 (2000).
R. T. Turner III, et al., "Subsite Specificity of Memapsin 2 (β-Secretase): Implications for Inhibitor Design," Biochemistry, 40:10001-10006 (2001).
Arun K. Ghosh, et al., "Structure Based Design: Potent Inhibitors of Human Brain Memapsin 2 (β-Secretase)," J. Med. Chem., 44:2865-2868 (2001).
A. K. Ghosh, et al., "β-Secretase as a Therapeutic Target for Inhibitor Drugs," Curr. Med. Chem., 9:1135-1144 (2002).
Robert T. Turner, III, "Specificity of Memapsin 1 and Its Implications on the Design of Memapsin 2 (β-Secretase) Inhibitor Selectivity," Biochemistry, 41:8742-8746 (2002).
Lin Hong, et al., "Crystal Structure of Memapsin 2 (β-Secretase) in Complex with an Inhibitor OM00-3," Biochemistry, 41:10963-10967 (2002).
L. Hong, et al., "Memapsin 2 (β-Secretase) as a therapeutic target," Biochem. Soc. Trans., 30:530-534 (2002).
Jordan Tang, et al., "Study of Memapsin 2 (β-Secretase) and Strategy of Inhibitor Design," Journal of Molecular Neuroscience, 20:299-304 (2003).
G. Koelsch, et al., "Memapsin 2, a drug target for Alzheimer's disease," Biochemical Society Symposia, 70:213-220 (2003).
W.-P. Chang, et al., "In vivo inhibition of Aβ production by memapsin 2 (β-secretase) inhibitors," J. Neurochem., 89:1409-1416 (2004).

(Continued)

*Primary Examiner* — Jeffrey Murray
(74) *Attorney, Agent, or Firm* — Barnes & Thornburg LLP

(57) ABSTRACT

There is provided a dihydroquinazoline compound of the formula

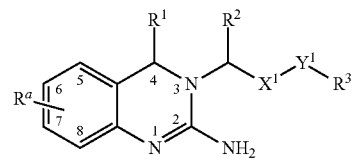

or a pharmaceutically acceptable salt thereof, wherein the values of the radicals are defined herein, as well as a pharmaceutical composition containing the compound, and a method of using the compound for the treatment of Alzheimer's disease.

20 Claims, No Drawings

OTHER PUBLICATIONS

Robert T. Turner, III, et al., "Structural Locations and Functional Roles of New Subsites $S_5$, $S_6$ and $S_7$ in Memapsin 2 (β-Secretase )," Biochemistry, 44:105-112 (2005).

Gerald Koelsch, et al., "Analysis of Amyloid Precursor Protein Processing Protease β-Secretase: Tools for Memapsin 2 (β-Secretase) Inhibition Studies," Amyloid Precursor Protein 41-50 (2005).

Arun K. Ghosh, et al., "Structure-based design of cycloamide-urethane-derived novel inhibitors of human brain memapsin 2 (β-secretase)," Bioorg. Med. Chem. Lett., 15:15-20 (2005).

Arun K. Ghosh, et al., "Recent Development of Structure-Based β-Secretase Inhibitors for Alzheimer's Disease," Curr. Top. Med. Chem., 5:1609-1622 (2005).

Arun K. Ghosh, et al., "Design, Synthesis and X-ray Structure of Protein-Ligand Complexes: Important Insight into Selectivity of Memapsin 2 (β-Secretase) Inhibitors," J. Am. Chem. Soc., 128:5310-5311 (2006).

Arun K. Ghosh, et al., "Design, Synthesis and X-ray Structure of Potent Memapsin 2 (β-Secretase) Inhibitors with Isophthalamide Derivatives as the $P_2$-$P_3$-Ligands," J. Med. Chem., 50:2399-2407 (2007).

Arun K. Ghosh, et al., "Memapsin 2 (β-Secretase) Inhibitor Drug, between Fantasy and Reality," Curr. Alz. Res., 4:418-422 (2007).

Arun K. Ghosh, et al., "Potent memapsin 2 (beta-secretase) inhibitors: Design, synthesis, protein-ligand X-ray structure, and in vivo evaluation," Bioorg. Med. Chem. Lett., 18:1031-1036 (2008).

Arun K. Ghosh, et al., "Memapsin 2 (Beta-Secretase) Inhibitors: Drug Development," Curr. Alz. Res., 5:121-131 (2008).

Arun K. Ghosh, et al., "β-Secretase as a Therapeutic Target for Alzheimer's Disease," Neurotherapeutics, 5:399-408 (2008).

PCT International Search Report/Written Opinion for PCT/US2009/065358, completed Jan. 5, 2010.

Polgar, et al., "Virtual Screening for Beta-Secretase (BACE1) Inhibitors Reveals the Importance of Protonation States at Asp32 and Asp228", 2005, Journal of Med. Chem., vol. 48, No. 11, pp. 3749-3755.

European Search Report and Annex for EP 09 82 8297, dated May 16, 2012, communicated May 23, 2012.

QUINAZOLINE INHIBITORS OF BACE 1 AND METHODS OF USING

CROSS REFERENCE TO RELATED APPLICATIONS

This application is a U.S. national application under 35 U.S.C. §371(b) of International Application Serial No. PCT/US2009/065358, filed Nov. 20, 2009, which claims priority under 35 USC §119(e) to U.S. Provisional Application Ser. No. 61/116,438 filed on Nov. 20, 2008 and U.S. Provisional Application Ser. No. 61/175,630 filed on May 5, 2009, the entire disclosure of each of which is incorporated herein by reference.

GOVERNMENT RIGHTS

This invention was made with government support under AG 18933 awarded by the National Institutes of Health. The government has certain rights in the invention.

BACKGROUND AND SUMMARY OF THE INVENTION

Alzheimer's disease is a progressive mental deterioration in a human resulting in loss of memory, confusion and disorientation, as well as, behavioral problems such as anxiety. Alzheimer's disease accounts for the majority of senile dementias and is a leading cause of death in adults. Currently-used treatments offer a small symptomatic benefit; no treatments to delay or halt the progression of the disease are as yet available.

The cause and progression of Alzheimer's disease are not well understood. Research indicates that the disease is associated with plaques and tangles in the brain. Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease and is a proteolytic fragment of amyloid precursor protein (APP). APP is cleaved initially by β-secretase (also referred to as BACE 1 or memapsin 2) followed by γ-secretase to generate Aβ. Without being bound by theory, it is believed that one approach to the treatment of Alzheimer's disease is to inhibit the production of Aβ.

It has been discovered herein that certain quinazoline compounds, such as the dihydroquinalozines described herein, and pharmaceutically acceptable salts of the foregoing may be used for treating Alzheimer's disease. In one illustrative embodiment of the invention, compounds and pharmaceutical compositions containing the compounds are described herein for treating patients in need of relief from Alzheimer's disease. In another embodiment, methods for treating Alzheimer's disease using the compounds and compositions are described herein. In another embodiment, uses of the compounds and compositions in the manufacture of medicaments for treating Alzheimer's disease are described herein. In one aspect, the compositions, methods, and medicaments include a therapeutically effective amount of one or more of the compounds described herein.

It is appreciated that the compounds described herein may be used alone or in combination with other compounds useful for treating such diseases, including those compounds that may operate by the same or different modes of action. It is appreciated that the compounds described herein may be used in combination with compounds to improve cognitive properties as well as anxiolytics and antipsychotics to control behavior.

DETAILED DESCRIPTION

In one embodiment, a compound of formula (I)

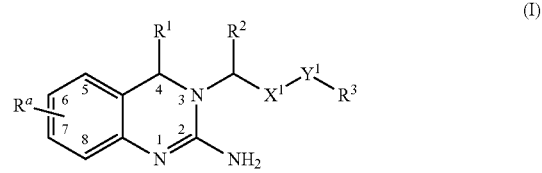

or a pharmaceutically acceptable salt, isomer, mixture of isomers, crystalline form, non crystalline form, hydrate, prodrug or solvate thereof is described; wherein $R^a$ is hydrogen; or $R^a$ represents one or more substituents independently selected from the group consisting of halogen, hydroxy, cyano, nitro, and optionally substituted alkyl, alkenyl, heteroalkyl, cycloalkyl, cycloalkenyl, heterocyclyl, aryl, arylalkyl, heteroaryl, heteroarylalkyl, alkoxy, aryloxy, acyl, acyloxy, alkoxycarbonyl, alkoxycarbonyloxy, alkylsulfonyl, arylsulfonyl, alkylsulfinyl, arylsulfinyl, carbamoyl, amido, carbamoyloxy, amino, and ureido; or $R^a$ represents two or more of said substituents, where two of said substituents are adjacent and taken together with the attached carbons to form a carbocycle or a heterocycle;

$R^1$ is hydrogen, or $R^1$ is alkyl, alkenyl, heteroalkyl, cycloalkyl, cycloalkenyl, heterocyclyl, aryl, arylalkyl, heteroaryl, or heteroarylalkyl, each of which is optionally substituted;

$R^2$ and $R^3$ are each independently selected from the group consisting of alkyl, alkenyl, heteroalkyl, cycloalkyl, cycloalkenyl, heterocyclyl, aryl, arylalkyl, heteroaryl, and heteroarylalkyl, each of which is optionally substituted; or $R^3$ and the attached nitrogen form an amino acid or derivative thereof;

$X^1$ is alkylene; and $Y^1$ is $N(R^4)$ or $OC(O)N(R^4)$;

$R^4$ is hydrogen, or $R^4$ is $X^2$—Z, where $X^2$ is a bond or an alkylene group; and Z is alkyl, alkenyl, heteroalkyl, cycloalkyl, cycloalkenyl, heterocyclyl, aryl, or heteroaryl, each of which is optionally substituted; or $R^3$ and $R^4$ are taken together with the attached nitrogen to form an optionally substituted heterocycle.

In another embodiment, a compound of the preceding embodiment wherein $X^1$—$Y^1$ is -alkylene-$N(R^4)$— is described. In another embodiment, a compound of the preceding embodiment wherein $X^1$—$Y^1$ is -alkylene-$OC(O)N(R^4)$— is described.

In another embodiment, a compound of the preceding embodiment wherein $X^1$—$Y^1$ is -alkylene-$N(R^4)$— and $R^1$ is hydrogen is described.

In another embodiment, a compound of the preceding embodiment wherein $X^1$—$Y^1$ is -alkylene-$OC(O)N(R^4)$— and $R^1$ is hydrogen is described.

In another embodiment, a compound of any of the preceding embodiments wherein $R^2$ is cycloalkyl or heterocyclyl, each of which is optionally substituted is described.

In another embodiment, a compound of any of the preceding embodiments wherein $X^1—Y^1$ has the formula

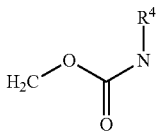

wherein $R^4$ is hydrogen, alkyl, or heteroarylalkyl, where heteroaryl is selected from the group consisting of thiazole, pyrazole, and oxazole, each of which is optionally substituted is described.

In another embodiment, a compound of any of the preceding embodiments wherein $X^1—Y^1$ has the formula

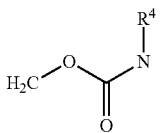

wherein $R^4$ is hydrogen, alkyl, or heteroarylalkyl, where heteroaryl is selected from the group consisting of thiazole and oxazole, each of which is optionally substituted is described.

In another embodiment, a compound of any of the preceding embodiments wherein $X^1—Y^1$ has the formula

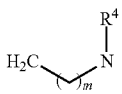

wherein $R^4$ is hydrogen, alkyl, or heteroarylalkyl, where heteroaryl is selected from the group consisting of thiazole and oxazole, each of which is optionally substituted; and m is 0, 1, 2, or 3 is described.

In another embodiment, a compound of any of the preceding embodiments wherein $X^1—Y^1$ has the formula

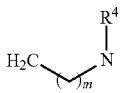

wherein $R^4$ is hydrogen, alkyl, or heteroarylalkyl, where heteroaryl is selected from the group consisting of thiazole, oxazole, and pyrazole, each of which is optionally substituted; and m is 0, 1, 2, or 3 is described.

In another embodiment, a compound of any of the preceding embodiments wherein $R^2$ is cycloalkyl or heterocycloalkyl, each of which is optionally substituted with hydroxy is described.

In another embodiment, a compound of any of the preceding embodiments wherein $R^3$ is cycloalkyl or heterocycloalkyl, each of which is optionally substituted with hydroxyl is described.

In another embodiment, a compound of any of the preceding embodiments wherein $R^3$ is cyclohexyl is described.

In another embodiment, a compound of any of the preceding embodiments wherein $R^3$ is cyclohexyl and $R^2$ is cyclohexyl is described.

In another embodiment, a compound of any of the preceding embodiments wherein $R^3$ is cyclohexyl, $R^2$ is cyclohexyl, and $R^a$ is 6-aryloxy is described.

In another embodiment, a compound of any of the preceding embodiments wherein $R^3$ is optionally substituted arylalkyl, such as benzyl, phenethyl, pheneth-1-yl, and the like is described.

In another embodiment, a compound of any of the preceding embodiments wherein $R^3$ is optionally substituted benzyl is described.

In another embodiment, a compound of any of the preceding embodiments wherein $R^3$ is optionally substituted aryl is described.

In another embodiment, a compound of any of the preceding embodiments wherein $R^3$ is cyclohexylmethyl is described.

In another embodiment, a compound of any of the preceding embodiments wherein $R^2$ is cyclohexyl is described.

In another embodiment, a compound of any of the preceding embodiments wherein $R^2$ is heteroaryl is described.

In another embodiment, a compound of any of the preceding embodiments wherein $R^2$ is selected from the group consisting of oxazole, isoxazole, thiazole, and isothiazole, each of which is optionally substituted, is described.

In another embodiment, a compound of any of the preceding embodiments wherein $R^2$ is cyclohexyl and $R^a$ is 6-aryloxy is described. In another embodiment, a compound of any of the preceding embodiments wherein $R^2$ is cyclohexyl, $R^a$ is 6-aryloxy, and m is 2 is described. In another embodiment, a compound of any of the preceding embodiments wherein $R^2$ is cyclohexyl, $R^a$ is 6-aryloxy, and $R^4$ is heteroarylalkyl. In another embodiment, a compound of any of the preceding embodiments wherein $R^4$ is an optionally substituted 4-oxazolylmethyl or an optionally substituted 2-thiazolylmethyl is described.

In another embodiment, a compound of any of the preceding embodiments wherein $R^2$ is tetrahydropyranyl or tetrahydrofuranyl is described.

In another embodiment, a compound of any of the preceding embodiments wherein $R^2$ cycloalkyl is described.

In another embodiment, a compound of any of the preceding embodiments wherein $R^a$ is 6-aryloxy is described.

In another embodiment, a compound of any of the preceding embodiments wherein $R^1$ is haloalkyl is described.

In another embodiment, a compound of any of the preceding embodiments wherein $R^2$ is haloalkyl is described.

In another embodiment, a compound of any of the preceding embodiments wherein $R^3$ is haloalkyl is described.

In another embodiment, a compound of any of the preceding embodiments wherein Z is haloalkyl is described.

In another embodiment, a compound of any of the preceding embodiments wherein $R^2$ is heterocyclyl, where the heterocyclyl is unsaturated is described.

In another embodiment, a compound of any of the preceding embodiments wherein $R^3$ is heterocyclyl, where the heterocyclyl is unsaturated is described.

In another embodiment, a compound of any of the preceding embodiments wherein Z is heterocyclyl, where the heterocyclyl is unsaturated is described.

In another embodiment, a compound of any of the preceding embodiments wherein $R^2$ is substituted with one or more substituents selected from the group consisting of halogen, hydroxy, alkoxy, haloalkoxy, aryloxy, acyloxy, alkoxycarbonyl, acyl, alkoxycarbonyloxy, alkylsulfonyl, arylsulfonyl, alkylsulfinyl, arylsulfinyl, optionally substituted carbamoyl, optionally substituted amido, optionally substituted carbamoyloxy, amino, optionally substituted ureido, and cyano is described.

In another embodiment, a compound of any of the preceding embodiments wherein $R^3$ is substituted with one or more substituents selected from the group consisting of halogen, hydroxy, alkoxy, haloalkoxy, aryloxy, acyloxy, alkoxycarbonyl, acyl, alkoxycarbonyloxy, alkylsulfonyl, arylsulfonyl, alkylsulfinyl, arylsulfinyl, optionally substituted carbamoyl, optionally substituted amido, optionally substituted carbamoyloxy, amino, optionally substituted ureido, and cyano is described.

In another embodiment, a compound of any of the preceding embodiments wherein $R^4$ is substituted with one or more substituents selected from the group consisting of halogen, hydroxy, alkoxy, haloalkoxy, aryloxy, acyloxy, alkoxycarbonyl, acyl, alkoxycarbonyloxy, alkylsulfonyl, arylsulfonyl, alkylsulfinyl, arylsulfinyl, optionally substituted carbamoyl, optionally substituted amido, optionally substituted carbamoyloxy, amino, optionally substituted ureido, and cyano is described.

In another embodiment, a compound of any of the preceding embodiments wherein $R^a$ is optionally substituted aryloxy is described.

In another embodiment, a compound of any of the preceding embodiments wherein $R^a$ is 6-aryloxy is described.

In another embodiment, a compound of any of the preceding embodiments wherein $R^1$ is hydrogen is described.

In another embodiment, a compound of any of the preceding embodiments wherein $R^2$ is cycloalkyl or heterocyclyl, each of which is optionally substituted is described.

In another embodiment, a compound of any of the preceding embodiments wherein $R^2$ is substituted with one or more substituents selected from the group consisting of halogen, hydroxy, alkoxy, haloalkoxy, aryloxy, acyloxy, alkoxycarbonyl, acyl, alkoxycarbonyloxy, alkylsulfonyl, arylsulfonyl, alkylsulfinyl, arylsulfinyl, optionally substituted carbamoyl, optionally substituted amido, optionally substituted carbamoyloxy, amino, optionally substituted ureido, and cyano is described.

In another embodiment, a compound of any of the preceding embodiments wherein $R^2$ is aryl or heteroaryl, each of which is optionally substituted is described.

In another embodiment, a compound of any of the preceding embodiments wherein $R^2$ is substituted with one or more substituents selected from the group consisting of halogen, hydroxy, alkoxy, haloalkoxy, aryloxy, acyloxy, alkoxycarbonyl, acyl, alkoxycarbonyloxy, alkylsulfonyl, arylsulfonyl, alkylsulfinyl, arylsulfinyl, optionally substituted carbamoyl, optionally substituted amido, optionally substituted carbamoyloxy, amino, optionally substituted ureido, and cyano is described.

In another embodiment, a compound of any of the preceding embodiments wherein $R^2$ is cycloalkyl or heterocyclyl, each of which is substituted with hydroxy is described.

In another embodiment, a compound of any of the preceding embodiments wherein $R^2$ is optionally substituted cyclohexyl is described.

In another embodiment, a compound of any of the preceding embodiments wherein $R^2$ is optionally substituted tetrahydropyranyl or tetrahydrofuranyl is described.

In another embodiment, a compound of any of the preceding embodiments wherein $R^2$ is hydroxy substituted cycloalkyl is described.

In another embodiment, a compound of any of the preceding embodiments wherein $R^2$ is optionally substituted heteroaryl is described.

In another embodiment, a compound of any of the preceding embodiments wherein $R^2$ is selected from the group consisting of oxazole, isoxazole, thiazole, and isothiazole, each of which is optionally substituted is described.

In another embodiment, a compound of any of the preceding embodiments wherein $R^3$ is cycloalkyl or heterocycloalkyl, each of which is substituted with hydroxyl is described.

In another embodiment, a compound of any of the preceding embodiments wherein $R^3$ is optionally substituted cyclohexyl is described.

In another embodiment, a compound of any of the preceding embodiments wherein $R^3$ optionally substituted phenyl, benzyl or phenethyl is described.

In another embodiment, a compound of any of the preceding embodiments wherein $R^3$ is optionally substituted cyclohexylmethyl or cyclohexylethyl is described.

In another embodiment, a compound of any of the preceding embodiments wherein $R^3$ is optionally substituted alkyl is described.

In another embodiment, a compound of any of the preceding embodiments wherein $R^3$ is optionally substituted heteroalkyl is described.

In another embodiment, a compound of any of the preceding embodiments wherein $R^3$ and the attached nitrogen form an amino acid or an ester or amide derivative thereof is described.

In another embodiment, a compound of any of the preceding embodiments wherein $R^3$ and the attached nitrogen form an amino acid or an ester or amide derivative thereof, and $R^4$ is hydrogen is described.

In another embodiment, a compound of any of the preceding embodiments wherein $R^3$ and the attached nitrogen form an ester or amide derivative of an amino acid, where the amino acid is selected from the group consisting of serine, threonine, and alkyl derivatives thereof is described.

In another embodiment, a compound of any of the preceding embodiments wherein $X^1$—$Y^1$ is alkylene-N($R^4$) is described.

In another embodiment, a compound of any of the preceding embodiments wherein alkylene is $C_1$-$C_4$ alkylene is described.

In another embodiment, a compound of any of the preceding embodiments wherein alkylene is $(CH_2)_2$ or $(CH_2)_3$ is described.

In another embodiment, a compound of any of the preceding embodiments wherein $X^1$—$Y^1$ is alkylene-OC(O)N($R^4$) is described.

In another embodiment, a compound of any of the preceding embodiments wherein $X^1$—$Y^1$ is methylene-OC(O)N($R^4$) is described.

In another embodiment, a compound of any of the preceding embodiments wherein $R^4$ is hydrogen, alkyl, or heteroarylalkyl In another embodiment, a compound of any of the preceding embodiments wherein $R^4$ is heteroarylalkyl, where the heteroaryl is selected from the group consisting of furan, pyrazole, thiazole and oxazole, each of which is optionally substituted is described.

In another embodiment, a compound of any of the preceding embodiments wherein $R^4$ is heteroarylalkyl, where the alkyl is selected from $CH_2$, $(CH_2)_2$, and $CH(CH_3)$ is described.

In another embodiment, a compound of any of the preceding embodiments wherein $R^4$ is optionally substituted heterocyclyl is described.

It is to be understood herein that divalent groups described herein may be included in the structures described herein in either orientation. Illustratively, when $Y^1$ is $OC(O)N(R^4)$, $X^1$ may be covalent bound to the oxygen or the nitrogen to form the carbamate or reverse carbamate.

It is to be understood that all combinations of the foregoing embodiments are also described herein. For example, in an illustrative variation, compounds of formula (I) are described where $X^1$—$Y^1$ is -alkylene-$OC(O)N(R^4)$—, $R^4$ is hydrogen, and $R^3$ and the attached nitrogen form an amino acid or derivative thereof. In another illustrative variation, compounds of formula (I) are described where $R^a$ is aryloxy, $R^4$ is optionally substituted heteroarylalkyl, and $R^3$ is cycloalkyl. All other combinations of the various embodiments are specifically described herein with reference to the foregoing.

In another embodiment, the following illustrative compounds are described.

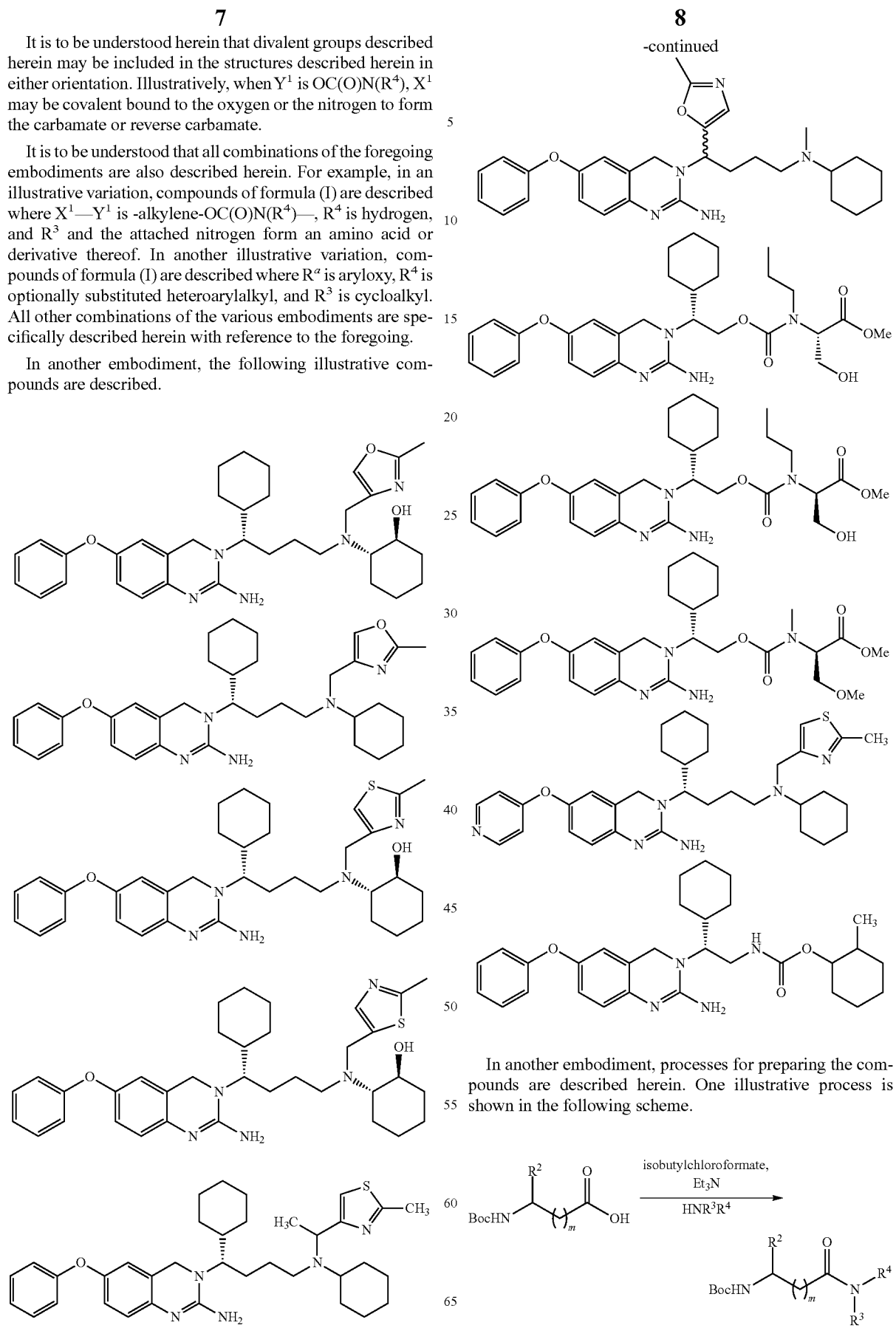

In another embodiment, processes for preparing the compounds are described herein. One illustrative process is shown in the following scheme.

-continued

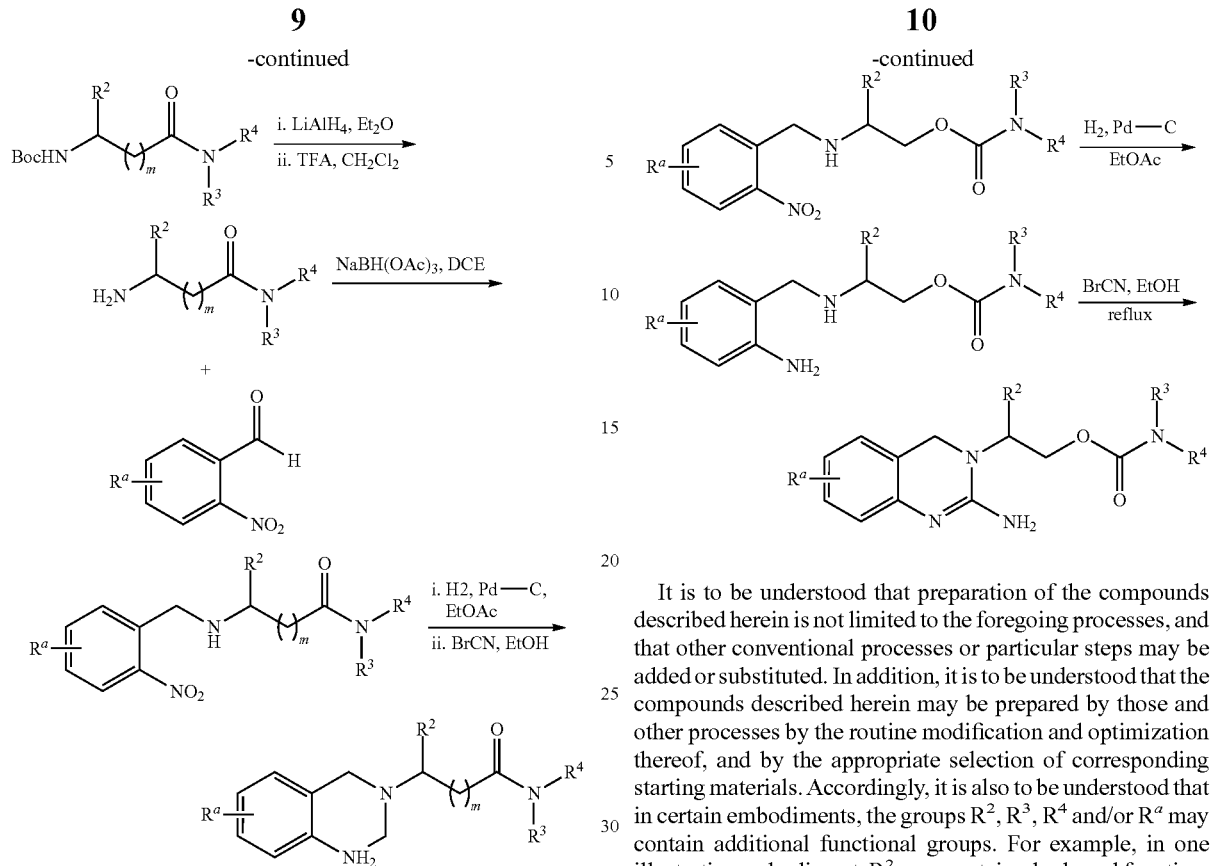

Another illustrative process is shown in the following scheme.

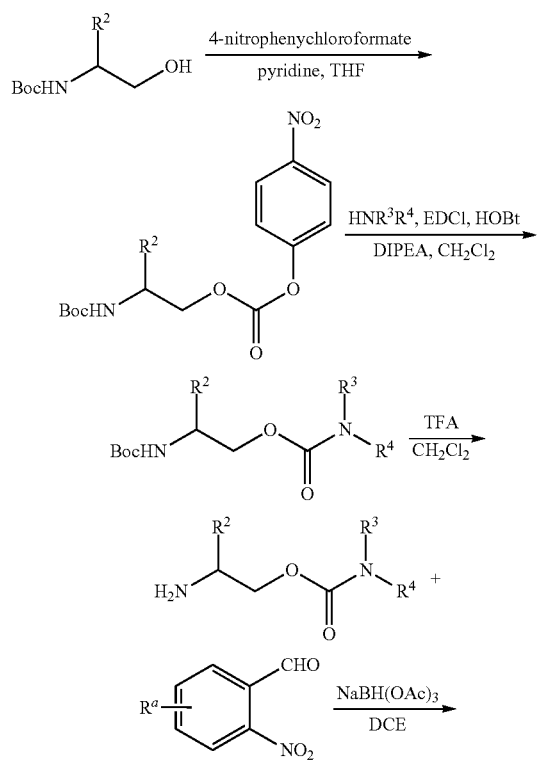

It is to be understood that preparation of the compounds described herein is not limited to the foregoing processes, and that other conventional processes or particular steps may be added or substituted. In addition, it is to be understood that the compounds described herein may be prepared by those and other processes by the routine modification and optimization thereof, and by the appropriate selection of corresponding starting materials. Accordingly, it is also to be understood that in certain embodiments, the groups $R^2$, $R^3$, $R^4$ and/or $R^a$ may contain additional functional groups. For example, in one illustrative embodiment, $R^2$ may contain a hydroxyl function. It is appreciated that protecting groups for such functional groups may be required and/or advantageously included in the process in one or more of the steps in the schemes shown above. Illustrative examples of protecting groups appear in Greene's Protective Groups in Organic Synthesis, 4th Edition, Peter G. M. Wuts and Theodora W. Greene, John Wiley & Sons, Inc., 2006.

In another embodiment, a method for treating a patient in need of relief from Alzheimer's disease is described herein. In one aspect, the method includes the step of administering to the patient a therapeutically effective amount of one or more compounds described herein, or a composition comprising one or more compounds described herein, such as those of any one of the preceding embodiments.

In another embodiment, the compounds and compositions described herein may be administered in a wide variety routes and dosage forms, including but not limited to oral, parenteral, topical, and like dosage forms. Illustratively, the compounds described herein may be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds described herein can be administered transdermally. Accordingly, the present invention also provides pharmaceutical compositions comprising a pharmaceutically acceptable diluent, carrier, and/or excipient and one or more compounds of the invention. It is appreciated that the selection of particular diluents, carriers and/or excipients are made with reference to the route of administration by routine optimization.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein may be formulated in a therapeutically effective amount in conventional dosage forms for the methods described herein, including one or more carriers, diluents, and/or excipients therefor. Such formulation compositions may be administered by a wide variety of conventional routes for the methods described herein in a wide variety of dosage formats, utilizing art-recognized products. See generally, Remington: The Science and Practice of Pharmacy, ($21^{st}$ ed., 2005).

The term "administering" as used herein refers to both local and systemic use, including but not limited to being taken or given orally, parenterally (including by subcutaneous, intramuscular, intravenous and intrathecal routes), by inhalation spray, by nasal, ocular, rectal, sublingual, or buccal routes, or topically, or the like in dosage form unit formulations containing conventional nontoxic pharmaceutically-acceptable carriers, adjuvants and vehicles.

Suitable routes for parenteral administration include intravenous, intraarterial, intraperitoneal, epidural, intraurethral, intrasternal, intramuscular and subcutaneous, as well as any other art recognized route of parenteral administration. Suitable means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier, or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

Examples of emulsifying agents that may be included in the formulations described herein are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Controlled release compositions for oral use may, e.g., be constructed to release the active drug by controlling the dissolution and/or the diffusion of the active drug substance. Illustrative sustained release formulations are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are incorporated herein by reference. The disclosure of each of the foregoing is incorporated herein by reference in its entirety. In addition, the entirety of the disclosure of each of the publications cited herein is also incorporated herein by reference.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

The pharmaceutical compositions described herein may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly (lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)).

For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

It is to be understood that an effective amount of any one or a mixture of the compounds or compositions described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

It is appreciated that compounds described herein can exist in unsolvated forms as well as solvated forms, including hydrated forms. It is to be understood that the solvated forms and the unsolvated forms and are described herein, either individually or collectively with reference to the compounds and compositions. It is also to be understood that the compounds described herein may exist in multiple amorphous, non-amorphous, partially crystalline, crystalline, and/or other morphological forms. In general, all physical forms are equivalent for the uses contemplated to be included in the invention described herein. It is also to be understood that the compounds described herein may be present in the form of a salt.

It is also appreciated that in the foregoing embodiments, certain aspects of the compounds are presented in the alternative, such as selections for any one or more of $X^1$, $X^2$, $Y^1$, Z, $R^1$, $R^2$, $R^3$, $R^4$, $R^a$, and m. It is therefore to be understood that various alternate embodiments of the invention include individual members of those lists, as well as the various subsets of those lists. Each of those combinations is to be understood to be described herein by way of the lists. In one illustrative example, $X^1$—$Y^1$ is $CH_2CH_2CH_2N(R^4)$, $R^1$ is hydrogen, $R^2$ is cyclohexyl, $R^3$ is cyclohexyl, $R^4$ is 3-tetrahydrofurylmethyl, and $R^a$ is 6-phenoxy.

The compounds described herein may also be present in the form of a prodrug. It is understood that prodrugs of the compounds described herein may be used in any of the uses of the compounds described herein. The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl, such as the aryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "alkyl" includes a chain of carbon atoms, which is optionally branched. It is to be understood that alkyl is advantageously of limited length, including $C_1-C_{24}$, $C_1-C_{12}$, $C_1-C_8$, $C_1-C_6$, and $C_1-C_4$. It is appreciated herein that shorter alkyl groups add less lipophilicity to the compound and accordingly will have different pharmacokinetic behavior.

As used herein, the term "cycloalkyl" includes an optionally branched chain of carbon atoms, where at least a portion of the chain forms one or more rings. In illustrative variations containing two rings, the rings may contain no common atoms, a single common atom, two adjacent common atoms, or more than two common atoms. It is to be understood that chain forming cycloalkyl is advantageously of limited length, including $C_3-C_{24}$, $C_3-C_{12}$, $C_3-C_8$, $C_3-C_6$, and $C_3-C_4$. It is appreciated herein that shorter alkyl groups add less lipophilicity to the compound and accordingly will have different pharmacokinetic behavior. As used herein, the term "cycloalkenyl" is a cycloalkyl group containing one or more unsaturated bonds.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium.

As used herein, the term "heterocyclyl" including heterocycle includes an optionally branched chain of atoms that includes both carbon and at least one heteroatom, where the chain optionally includes one or more unsaturated bonds, and where at least a portion of the chain forms one or more rings. As used herein, it is understood that the term "heterocyclyl" also includes "heterocycloalkyl" and "cycloheteroalkyl." Illustrative heteroatoms include nitrogen, oxygen, and sulfur. In certain variations, illustrative heteroatoms also include phosphorus, and selenium. Illustrative heterocyclyls include, but are not limited to, tetrahydrofuryl, bis(tetrahydrofuranyl), pyrrolidinyl, tetrahydropyranyl, piperidinyl, morpholinyl, piperazinyl, homopiperazinyl, quinuclidinyl, dihydrofuryl, pyrrolinyl, dihydropyranyl, and the like. It is also to be understood that heterocyclyl includes polycyclic radicals, including fused bicycles, spiro bicycles, and the like.

As used herein, the term "aryl" includes monocyclic and polycyclic aromatic carbocyclic and aromatic heterocyclic groups, each of which may be optionally substituted. As used herein, the term "heteroaryl" includes aromatic heterocyclic groups, each of which may be optionally substituted. Illustrative carbocyclic aromatic groups described herein include, but are not limited to, phenyl, naphthyl, and the like. Illustrative heterocyclic aromatic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group NH$_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "optionally substituted amino" includes derivatives of amino as described herein, such as, but not limited to, acylamino, urea, and carbamate, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

The term "optionally substituted aryl" as used herein includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

As used herein the term "amino acid", refers to a moiety including the general formula:

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like As used herein, alkylene is taken to mean an optionally substituted bivalent hydrocarbon group wherein the hydrocarbon group may be a branched hydrocarbon group. Non-limiting, illustrative examples include methylene, 1,2-ethylene, 1-methyl-1,2-ethylene, 1,4-butylene, 2,3-dimethyl-1,4-butylene, 2-methyl-2-ethyl-1,5-pentylene, and the like. Heteroalkylene is taken to mean an alkylene group wherein one or more carbon atoms are replaced with a heteroatom selected from oxygen, sulfur or optionally substituted nitrogen.

As used herein, haloalkyl is taken to mean an alkyl group wherein one or more hydrogen atoms is replaced with a halogen atom, independently selected in each instance from the group consisting of fluorine, chlorine, bromine and iodine. Non-limiting, illustrative examples include, difluoromethyl, 2,2,2-trifluoroethyl, 2-chlorobutyl, 2-chloro-2-propyl, 1,1,1-trifluoro-2-butyl, trifluoromethyl, bromodifluoromethyl, and the like.

As used herein, pharmaceutically acceptable salts include acid addition salts, base addition salts, and hemisalts. Suitable acid addition salts, include but are not limited to, those formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts, include but are not limited to, those formed from bases which form non-toxic salts. Illustrative examples include the aluminium, arginine, benzathine, calcium, choline, diethylamine, diolamine, glycine, lysine, magnesium, meglumine, olamine, potassium, sodium, tromethamine and zinc salts.

As used herein, references to hemisalts of acids and bases, include but are not limited to, those formed from, for example, hemisulphate and hemicalcium salts.

Additional features of the present invention will become apparent to those skilled in the art upon consideration of the following description of illustrative embodiments for carrying out the invention.

METHODS AND EXAMPLES

Example 1

Synthesis Of Compound 0458. The process in the following scheme is followed.

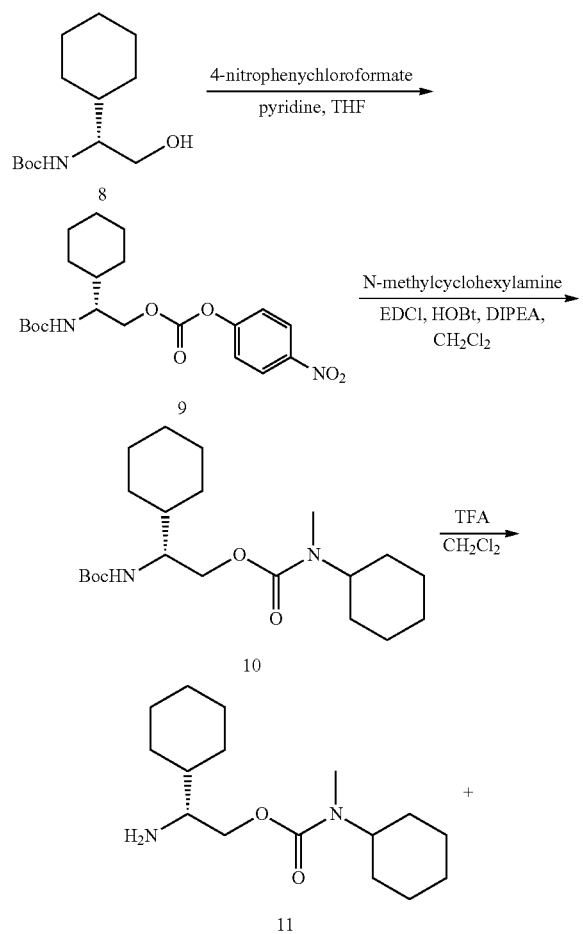

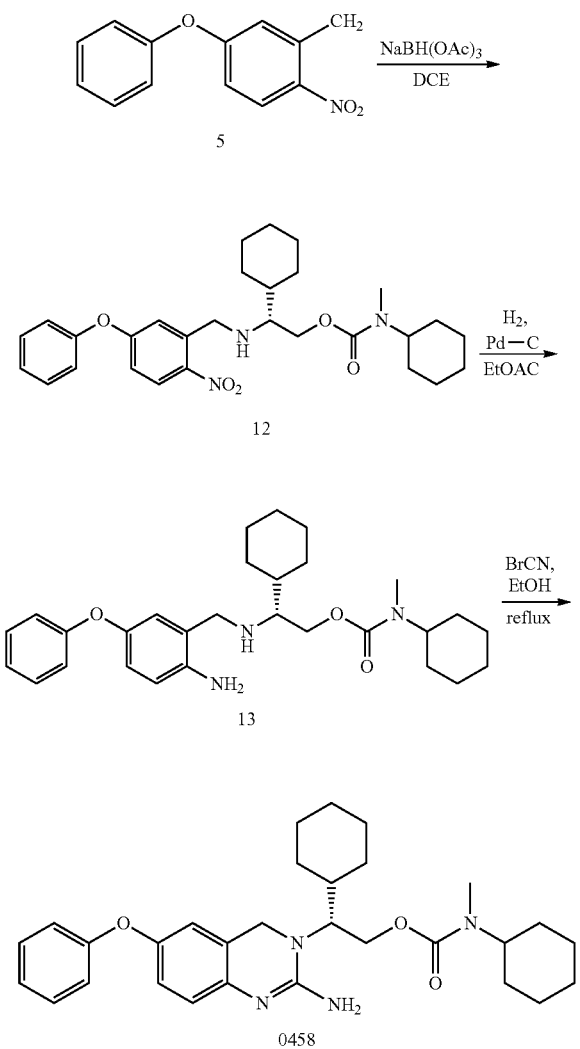

To a stirred solution of 8 (Catalano et. al. Bioorg. Med. Chem. Lett. 2004, 14, 275) (220 mg, 0.9 mmol) in dry THF (3 mL), p-nitrophenylchloroformate (206 mg, 0.99 mol) and pyridine (100 μL) were added and the resulting mixture was stirred at 23° C. for 12 h. The mixture was concentrated under reduced pressure and the residue was passed through a short silica gel column (eluted with 25% ethyl acetate in hexane) to provide carbonate 9. This carbonate was then reacted with N-methylcyclohexylamine (130 μL, 1 mmol) in the presence of $Et_3N$ (125 μL) at 23° C. for 12 h. Standard workup and chromatography over silica gel with 30% ethyl acetate in hexane provided urethane 10 (391 mg).

Urethane 10 (391 mg) was dissolved in $CH_2Cl_2$ (1 mL) and the mixture was cooled to 0° C. and trifluoroacetic acid (3 mL) was added. The mixture was warmed to 23° C. and stirred for 2 h. Evaporation of solvents and column chromatography over silica gel with 1-5% MeOH in $CH_2Cl_2$ provided amine 11.

To a stirred solution amine 11 (87 mg, 0.31 mmol) and aldehyde 5 (75 mg, 0.31 mmol) in dichloroethane (2 mL), $NaBH(OAc)_3$ (131 mg, 0.6 mmol) was added and the resulting mixture was stirred at 23° C. for 12 h. The reaction was quenched with aqueous $NaHCO_3$ solution and standard workup followed by chromatography over silica gel using 1% MeOH in $CH_2Cl_2$ provided amine 12 (121 mg).

Amine 12 (121 mg) was dissolved in ethyl acetate (3 mL) and 10% Pd—C (30 mg) was added to it. The mixture was then hydrogenated under a hydrogen filled balloon for 4 h. The reaction mixture was filtered through a pad of celite and the residue was passed through a short silica gel column using 5% MeOH in $CHCl_3$ as the eluting solvent to provide diamine 13 (100 mg).

Amine 13 (100 mg, 0.2 mmol) was dissolved in ethanol (3 mL) and BrCN (44 mg, 0.4 mmol) was added. The resulting mixture was heated under reflux for 4 h. The reaction was cooled to 23° C. and the mixture was concentrated under reduced pressure to give a residue. The residue was chromatographed over silica gel using 1-5% MeOH in $CH_2Cl_2$ to provide urethane 0458 (60 mg).

Example 2

Synthesis of Carbamate 0538. The process in the following scheme is followed.

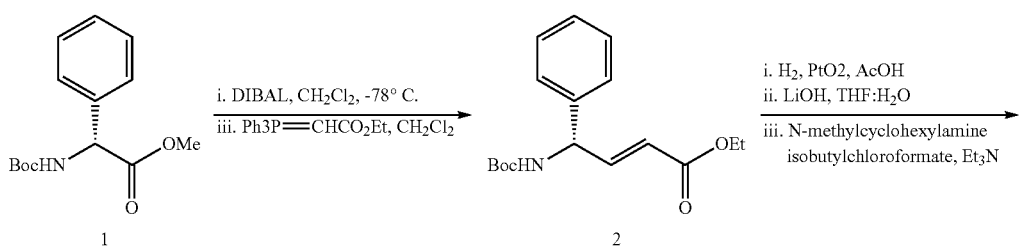

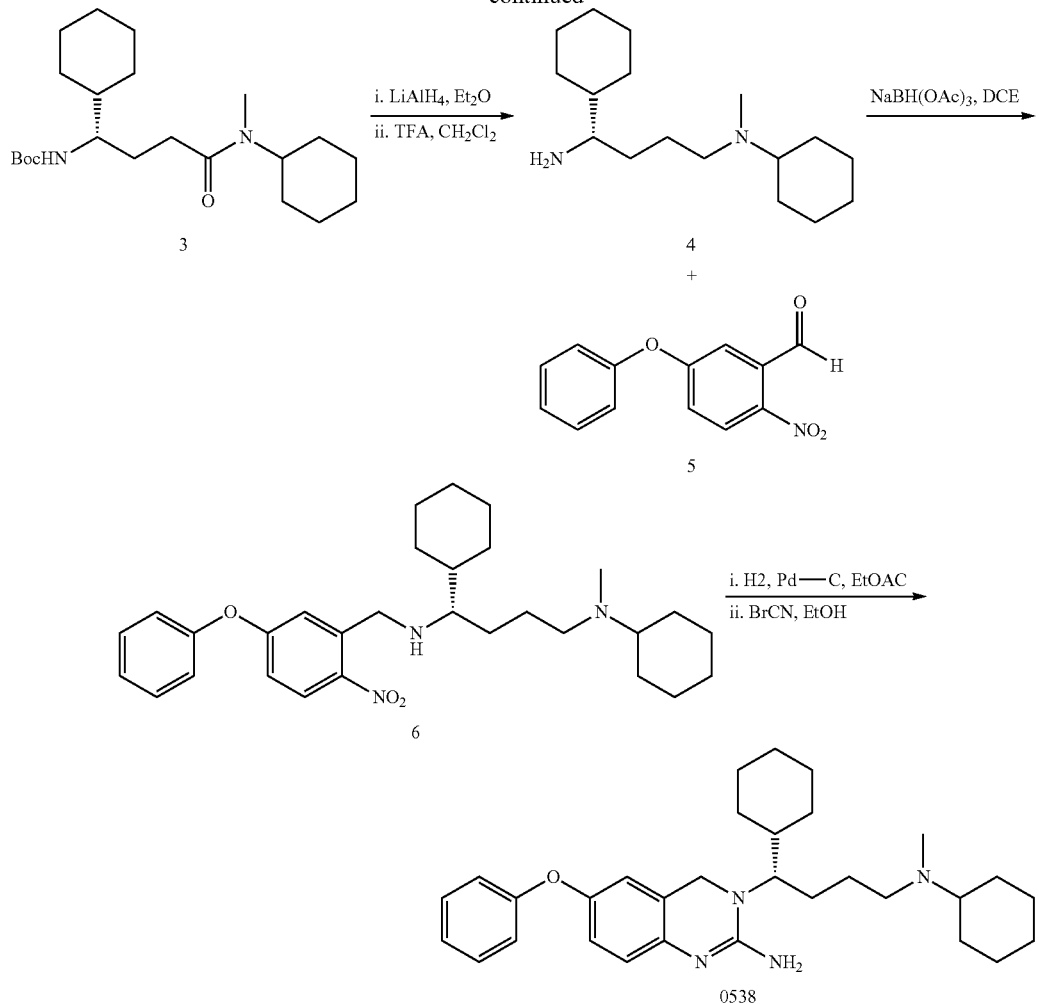

Phenylglycine methyl ester 1 (6.28 g, 23.3 mmol) was dissolved in CH$_2$CL$_2$ (50 mL) and the mixture was cooled to −78° C. To this mixture, DIBAL-H (47 mL) in CH$_2$Cl$_2$ was added and mixture was stirred at −78° C. for 15 min and then quenched with MeOH and aqueous sodium tartrate and resulting mixture was extracted with CH$_2$Cl$_2$, washed with brine and solvent was evaporated. The residue containing crude aldehyde was used directly without further purification. The aldehyde was dissolved in CH$_2$Cl$_2$, (100 mL) and Ph$_3$P=CHCO$_2$Et (8 g) was added. The resulting mixture was stirred at 23° C. for 12 h. The mixture was concentrated under reduced pressure and residue was loaded on a short silica gel column (eluted with 25% ethyl acetate in hexane) to provide unsaturated ester 2 (2.5 g).

Unsaturated ester 2 (512 mg) was dissolved in acetic acid (10 mL) and PtO$_2$ (30 mg) was added. The mixture as then hydrogenated under 40 psi for 16 h. The catalyst was filtered off by passing through a pad of Celite. The solvent was evaporated to provide the corresponding saturated cyclohexyl derivative in quantitative yield. To a stirred solution of this ester (480 mg, 1.5 mmol) in THF (3 mL), solid LiOH (320 mg) followed by water (1 mL) and methanol (1 mL) were added. The mixture was stirred overnight. The mixture was cooled to 0° C. and acidified to pH 3 using dilute HCl. The mixture was extracted with ethyl acetate, dried over Na$_2$SO$_4$ and concentrated to provide the acid which was used without further purification. The acid (390 mg) was dissolved in CH$_2$Cl$_2$ (6 mL) and EDC (522 mg, 2.7 mmol), HOBt (369 mg, 2.7 mmol) N-methylcyclohexylamine (250 µL) and diisopropylethylamine (2 mL) were added. The resulting mixture was stirred at 23° C. for 12 h. The reaction was quenched with saturated NaHCO$_3$ solution and was extracted with ethyl acetate and dried over Na$_2$SO$_4$. Evaporation of solvent gave a residue which was chromatographed to provide amine 3.

To a stirred solution of amine 3 (126 mg, 0.33 mmol) in Et$_2$O (2 mL) at 0° C., LAH (25 mg, 0.66 mmol) was added. The mixture was stirred at 0° C. to 23° C. for 4 h. The reaction was quenched with excess of ethyl acetate and stirred for 15 min. Brine was added and the mixture was extracted with ethyl acetate, dried over Na$_2$SO$_4$ and concentrated to provide the amine which was used without further purification. To a solution of the amine (70 mg) in CH$_2$CL$_2$ (2 mL), CF$_3$CO$_2$H (0.6 mL) was added and the mixture was stirred at 23° C. for 3 h. Evaporation of solvent and column chromatography over a short silica gel provided the diamine 4.

To a stirred solution of diamine 4 (66 mg, 0.23 mmol) and aldehyde 5 (69 mg, 0.28 mmol) in dichloroethane (2 mL) NaBH(OAc)$_3$ (100 mg, 0.47 mmol) was added and the resulting mixture was stirred at 23° C. for 12 h. The reaction was quenched with aqueous NaHCO$_3$ solution and standard workup followed by chromatography over silica gel using 1-10% MeOH in CH₂Cl₂ provided amine 6.

Amine 6 (34 mg) was dissolved in ethyl acetate (2 mL) and 10% Pd—C (10 mg) was added to it. The mixture was then hydrogenated under a hydrogen filled balloon for 4 h. The reaction mixture was filtered through a pad of celite and the residue was passed through a short silica gel column using 5% MeOH in CHCl₃ as the eluting solvent to provide the corresponding aniline derivative. The aniline derivative (13 mg, 0.03 mmol) was dissolved in ethanol (3 mL) and BrCN (5 mg, 0.04 mmol) was added. The resulting mixture was heated under reflux for 4 h. The reaction was cooled to 23° C. and the mixture was concentrated under reduced pressure to give residue. The residue was chromatographed over silica gel using 5% MeOH in CH₂Cl₂ to provide amine derivative 0538 (8 mg).

Method Example

Inhibition Of Memapsin 2. Without being bound by theory, it is believed that the compounds herein described exert their effect on Alzheimer's disease by inhibiting the proteolytic activity of the enzyme memapsin 2. Potency of compounds were determined by measurement of their inhibition of memapsin 2 catalytic activity toward a fluorescent substrate. Kinetic inhibition experiments were performed using the procedure as described in Ermolieff, et al. (Biochemistry 39:12450-12456 (2000), the teachings of which are incorporated hereby in their entirety). Briefly, assays were performed at pH 4, 37° C., by pre-incubation of memapsin 2 enzyme with compound for 20 minutes. Activity measure was initiated by addition of a fluorogenic substrate FS-2 (Bachem Americas, Torrance, Calif.). Fluorescent signal increase over time was measured as a rate of hydrolysis of the peptide substrate. Inhibition of hydrolytic rate was expressed relative to uninhibited controls and fit to a model for tight-binding inhibitors (J. Bieth, in "Proteinase Inhibitors," Bayer Symposium V, 463-469, 1974). Illustrative activity of the compounds described herein is shown in TABLE 1.

TABLE 1

| Inhibitor | Structure | MW | Activity[a] |
|---|---|---|---|
| 119 | 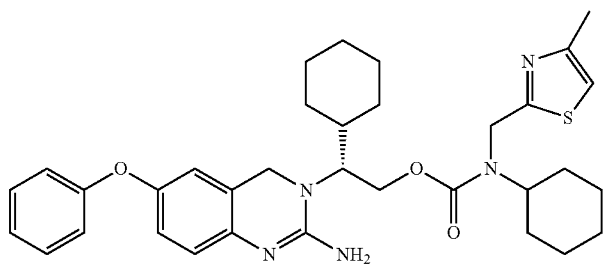 [SMILES: Cc1csc(CN(C(=O)OC[C@@H](C2CCCCC2)N2Cc3cc(Oc4ccccc4)ccc3N=C2N)C2CCCCC2)n1] | 602 | ++ |
| 0188 | 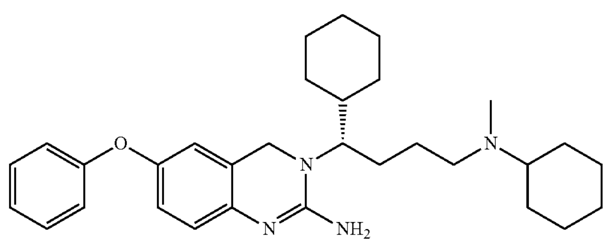 [SMILES: CN(CCC[C@@H](C1CCCCC1)N1Cc2cc(Oc3ccccc3)ccc2N=C1N)C1CCCCC1] | 489 | +++ (+++) |
| 0318 | 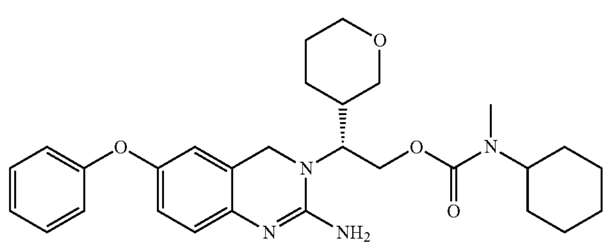 | 507 | ++ (+) |
| 0328 | 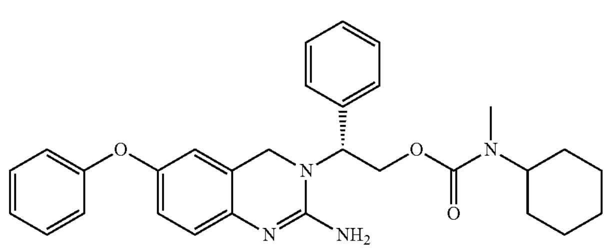 [SMILES: CN(C(=O)OC[C@@H](c1ccccc1)N1Cc2cc(Oc3ccccc3)ccc2N=C1N)C1CCCCC1] | 499 | + (+) |

TABLE 1-continued

| Inhibitor | Structure | MW | Activity[a] |
|---|---|---|---|
| 0408 | 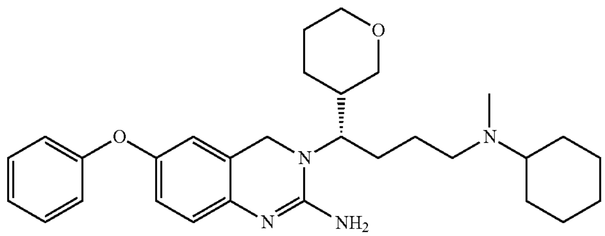 | 491 | ++ |
| 409 | 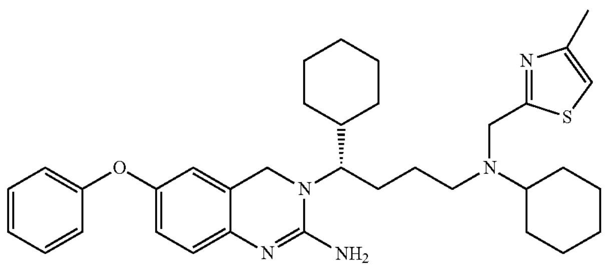 [SMILES: Cc1csc(CN(CCC[C@@H](C2CCCCC2)N2Cc3cc(Oc4ccccc4)ccc3N=C2N)C2CCCCC2)n1] | 586 | ++ |
| 0418 | 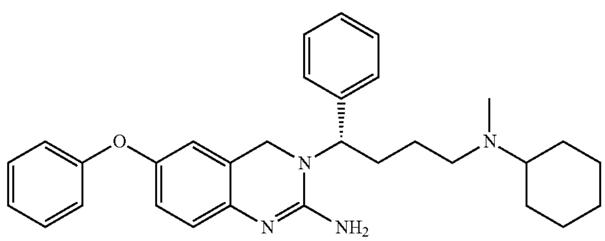 [SMILES: CN(CCC[C@@H](c1ccccc1)N1Cc2cc(Oc3ccccc3)ccc2N=C1N)C1CCCCC1] | 483 | + (+) |
| 0428 | 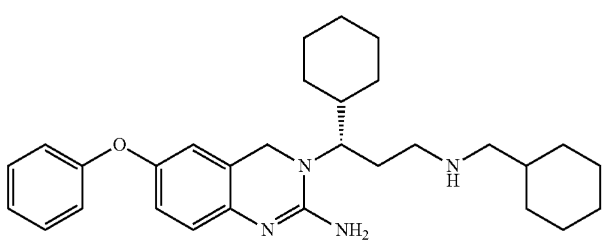 [SMILES: NC1=Nc2ccc(Oc3ccccc3)cc2CN1[C@@H](CCNCC1CCCCC1)C1CCCCC1] | 475 | ++ |
| 0438 | 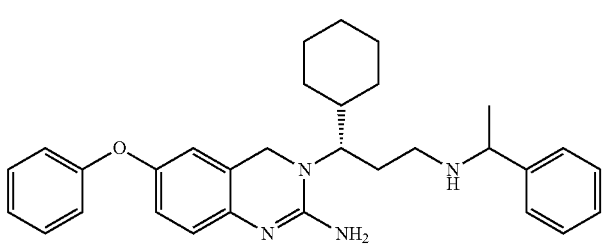 | 483 | ++ |
| 0448 | 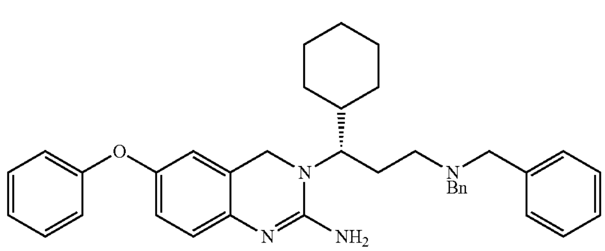 [SMILES: CC(NCC[C@@H](C1CCCCC1)N1Cc2cc(Oc3ccccc3)ccc2N=C1N)c1ccccc1] | 559 | ++ (+) |

TABLE 1-continued

| Inhibitor | Structure | MW | Activity[a] |
|---|---|---|---|
| 0458 | 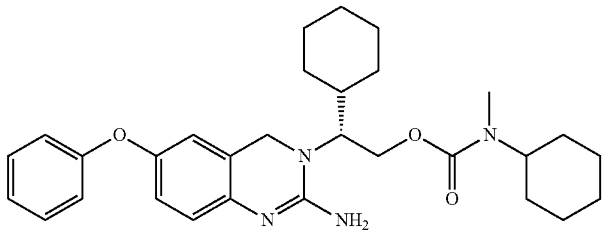 [SMILES: CN(C(=O)OC[C@@H](C1CCCCC1)N1Cc2cc(Oc3ccccc3)ccc2N=C1N)C1CCCCC1] | 505 | +++ (−) |
| 0538 | 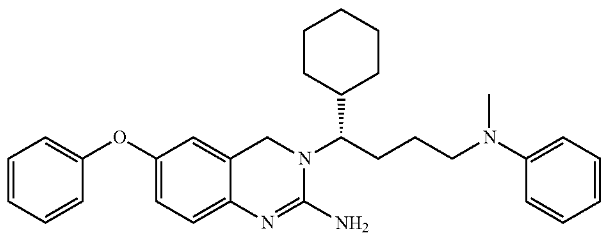 | 483 | ++ |
| 0548 | 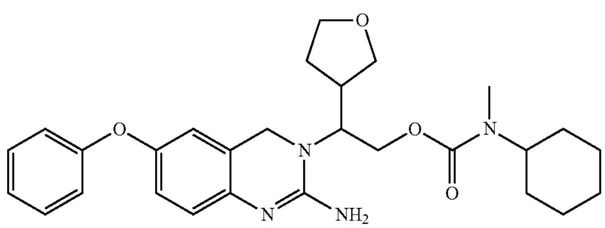 [SMILES: CN(C(=O)OCC(C1CCOC1)N1Cc2cc(Oc3ccccc3)ccc2N=C1N)C1CCCCC1] | 493 | ++ (+) |
| 0568 | 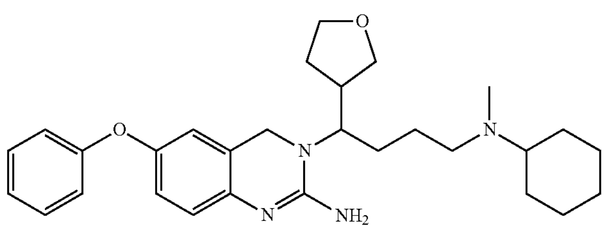 [SMILES: CN(CCCC(C1CCOC1)N1Cc2cc(Oc3ccccc3)ccc2N=C1N)C1CCCCC1] | 477 | ++ |
| 0618 | 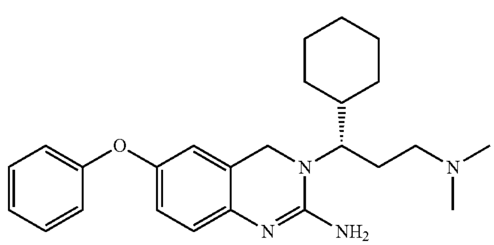 [SMILES: CN(C)CC[C@@H](C1CCCCC1)N1Cc2cc(Oc3ccccc3)ccc2N=C1N] | 407 | + |
| 0628 | 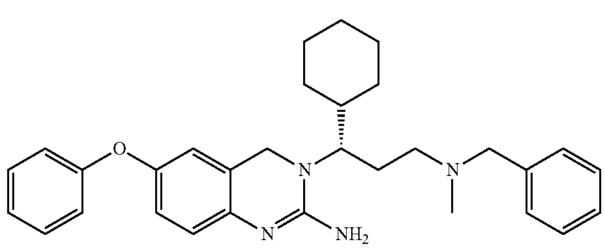 [SMILES: CN(CC[C@@H](C1CCCCC1)N1Cc2cc(Oc3ccccc3)ccc2N=C1N)Cc1ccccc1] | 483 | ++ |

TABLE 1-continued

| Inhibitor | Structure | MW | Activity[a] |
|---|---|---|---|
| 0648 | 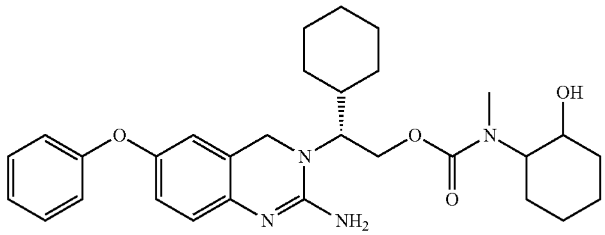 [SMILES: CN(C(=O)OC[C@@H](C1CCCCC1)N1Cc2cc(Oc3ccccc3)ccc2N=C1N)C1CCCCC1O] | 521 | ++ |
| 0658 | 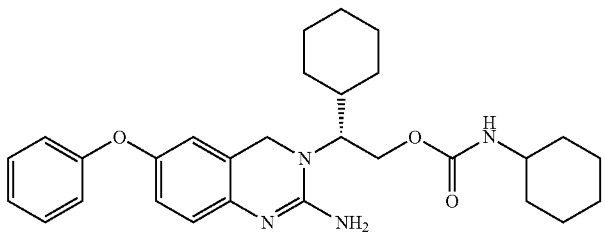 [SMILES: NC1=Nc2ccc(Oc3ccccc3)cc2CN1[C@@H](COC(=O)NC1CCCCC1)C1CCCCC1] | 491 | ++ |
| 0668 | 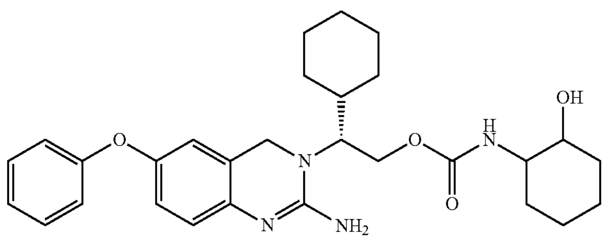 [SMILES: NC1=Nc2ccc(Oc3ccccc3)cc2CN1[C@@H](COC(=O)NC1CCCCC1O)C1CCCCC1] | 507 | ++ |
| 908 | 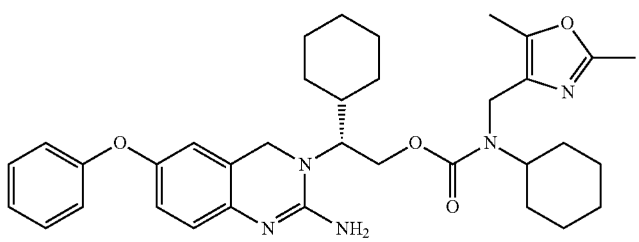 [SMILES: Cc1nc(CN(C(=O)OC[C@@H](C2CCCCC2)N2Cc3cc(Oc4ccccc4)ccc3N=C2N)C2CCCCC2)c(C)o1] | 600 | ++ |
| 0469 | 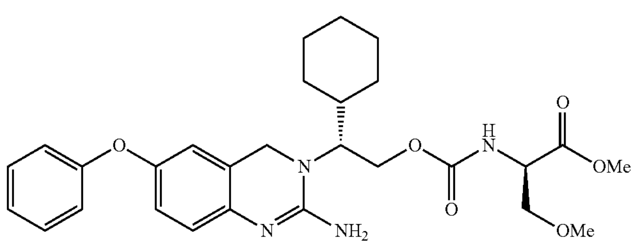 [SMILES: COC[C@@H](NC(=O)OC[C@@H](C1CCCCC1)N1Cc2cc(Oc3ccccc3)ccc2N=C1N)C(=O)OC] | 525 | ++ |
| 0509 | 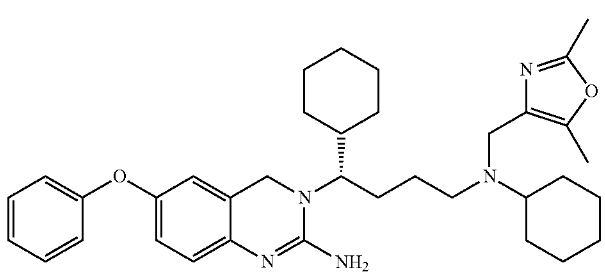 [SMILES: Cc1nc(CN(CCC[C@@H](C2CCCCC2)N2Cc3cc(Oc4ccccc4)ccc3N=C2N)C2CCCCC2)c(C)o1] | 584 | ++ |

TABLE 1-continued

| Inhibitor | Structure | MW | Activity[a] |
|---|---|---|---|
| 0519 | 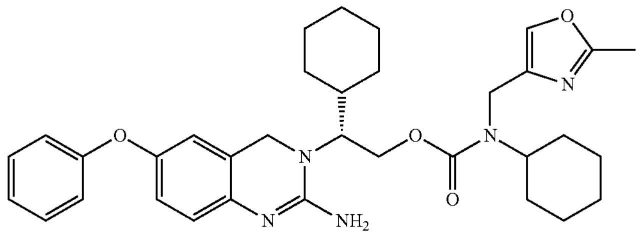 | 586 | + |
| 0579 | 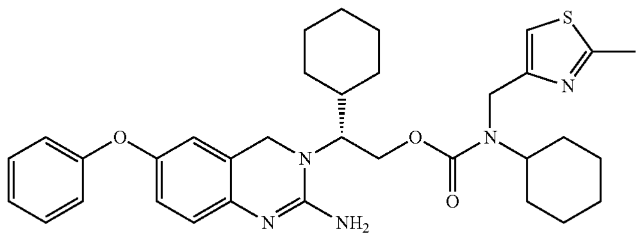 [SMILES: Cc1nc(CN(C(=O)OC[C@@H](C2CCCCC2)N2Cc3cc(Oc4ccccc4)ccc3N=C2N)C2CCCCC2)co1] | 601 | + |
| 0589 | 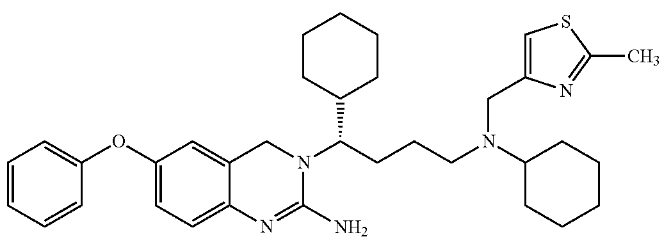 | 586 | ++ |
| 0659 | 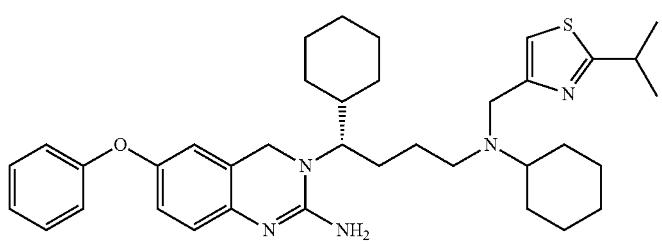 [SMILES: CC(C)c1nc(CN(CCC[C@@H](C2CCCCC2)N2Cc3cc(Oc4ccccc4)ccc3N=C2N)C2CCCCC2)cs1] | 614 | ++ |
| 0789 | 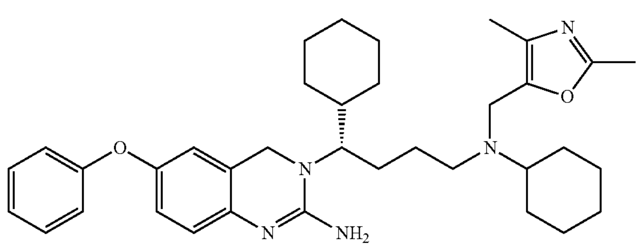 [SMILES: Cc1nc(C)c(CN(CCC[C@@H](C2CCCCC2)N2Cc3cc(Oc4ccccc4)ccc3N=C2N)C2CCCCC2)o1] | 584 | ++ |
| 0809 | 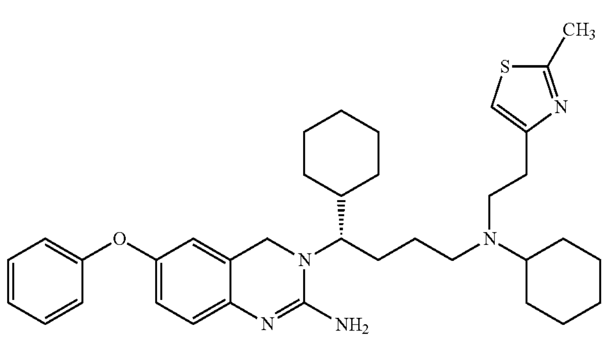 [SMILES: Cc1nc(CCN(CCC[C@@H](C2CCCCC2)N2Cc3cc(Oc4ccccc4)ccc3N=C2N)C2CCCCC2)cs1] | 600 | ++ |

TABLE 1-continued
| Inhibitor | Structure | MW | Activity[a] |
|---|---|---|---|
| 0909 | 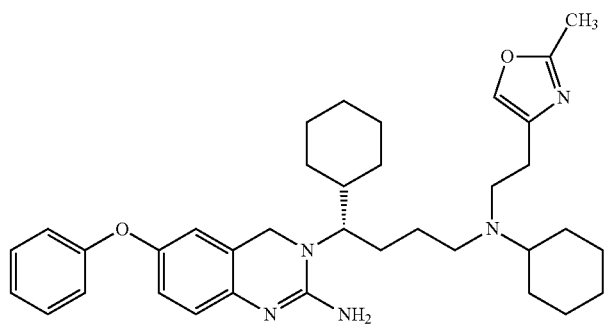 | 584 | ++ |
| 0929 | 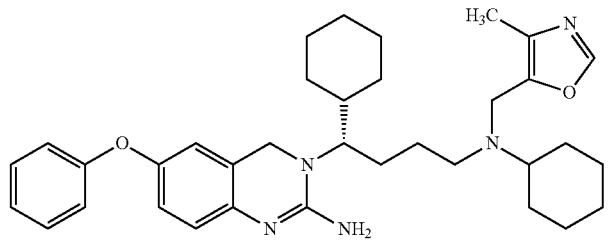 [SMILES: Cc1ncoc1CN(CCC[C@@H](C1CCCCC1)N1Cc2cc(Oc3ccccc3)ccc2N=C1N)C1CCCCC1] | 570 | ++ |
| 0979 | 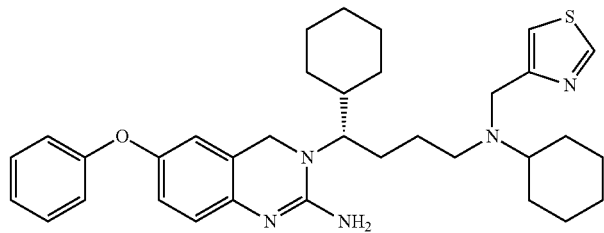 [SMILES: NC1=Nc2ccc(Oc3ccccc3)cc2CN1[C@@H](CCCN(Cc1cscn1)C1CCCCC1)C1CCCCC1] | 572 | ++ |
| 0989 | 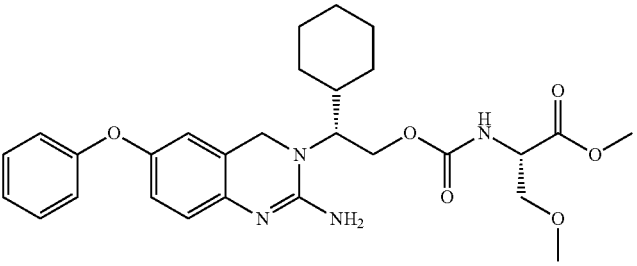 [SMILES: COC[C@H](NC(=O)OC[C@@H](C1CCCCC1)N1Cc2cc(Oc3ccccc3)ccc2N=C1N)C(=O)OC] | 525 | ++ |
| 1049 | 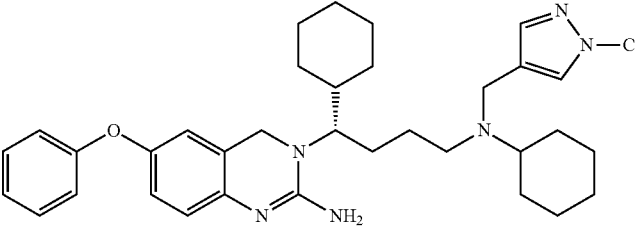 | 569 | ++ |
| 1099 | 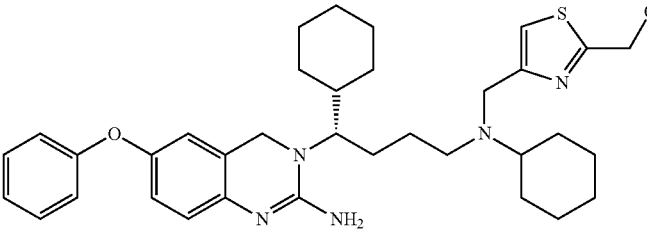 | 616 | ++ |

TABLE 1-continued

| Inhibitor | Structure | MW | Activity[a] |
|---|---|---|---|
| 1139 | 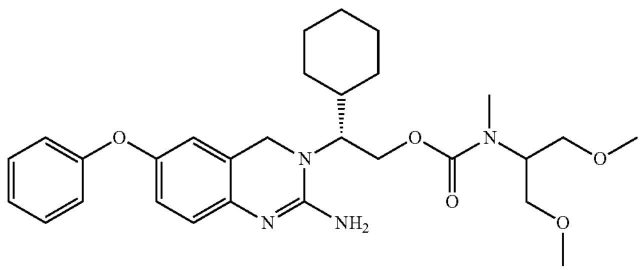 [SMILES: COCC(COC)N(C)C(=O)OC[C@@H](C1CCCCC1)N1Cc2cc(Oc3ccccc3)ccc2N=C1N] | 525 | + |
| 1209 | 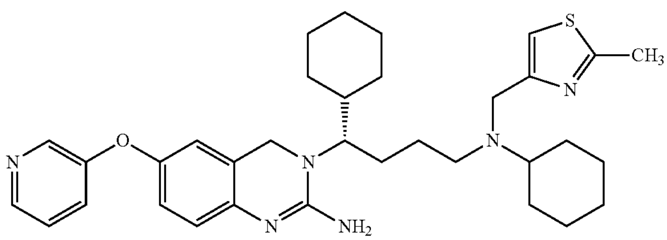 [SMILES: Cc1nc(CN(CCC[C@@H](C2CCCCC2)N2Cc3cc(Oc4cccnc4)ccc3N=C2N)C2CCCCC2)cs1] | 587 | + |
| 1219 | 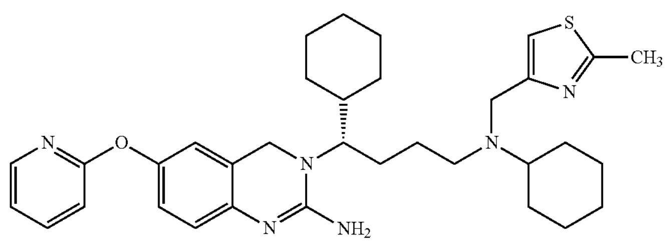 [SMILES: Cc1nc(CN(CCC[C@@H](C2CCCCC2)N2Cc3cc(Oc4ccccn4)ccc3N=C2N)C2CCCCC2)cs1] | 587 | + |
| 1379 | 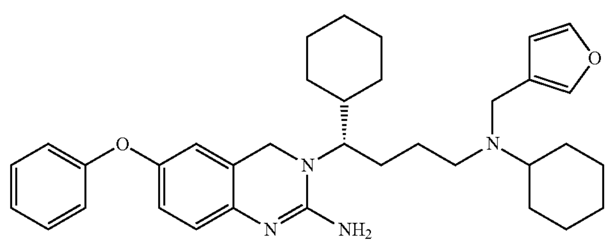 [SMILES: NC1=Nc2ccc(Oc3ccccc3)cc2CN1[C@@H](CCCN(Cc1ccoc1)C1CCCCC1)C1CCCCC1] | 555 | ++ |
| 1509 | 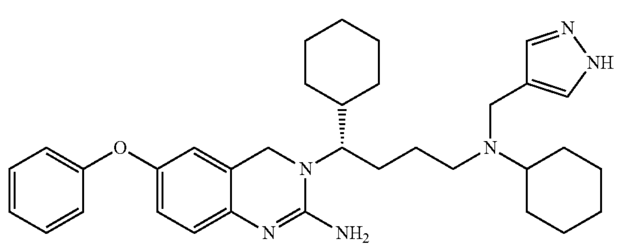 [SMILES: NC1=Nc2ccc(Oc3ccccc3)cc2CN1[C@@H](CCCN(Cc1cn[nH]c1)C1CCCCC1)C1CCCCC1] | 555 | +++ |
| 1519 | 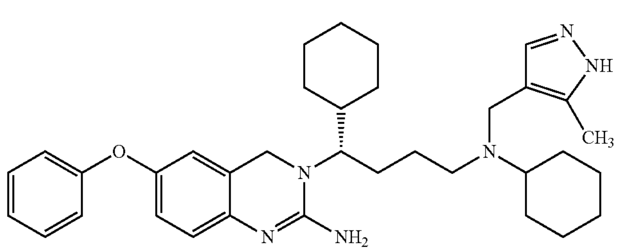 [SMILES: Cc1[nH]ncc1CN(CCC[C@@H](C1CCCCC1)N1Cc2cc(Oc3ccccc3)ccc2N=C1N)C1CCCCC1] | 569 | +++ |

[a]Activity against memapsin 2: $K_i$ ($IC_{50}$) >5 μM, −; <5 μM, +; <500 nM, ++; <50 nM, +++

Method Example

Inhibition of Memapsin 1, Memapsin 2, and Cathepsin D Catalytic Activity. A substrate peptide H$_3$N-ELDLAVEF-WHDR-CO$_2$ (used for inhibition assay of memapsin 2, memapsin 1, and cathepsin D) is dissolved at 2 mg/ml in DMSO and diluted 1:100 in 0.1 M sodium acetate, pH 4.0 just prior to assay. Inhibitor dissolved in DMSO is diluted into 0.1 M sodium acetate, pH 4.0 (1:100 dilution). A 50 µl aliquot of the inhibitor solution in pH 4 buffer is combined with 150 µl of 0.1 M sodium acetate containing 100-200 nM of memapsin 1, memapsin 2, or cathepsin D. Following a pre-incubation at 37° C., the proteolytic assay is initiated by addition of 50 µl of the substrate diluted into pH 4 buffer, and incubation continued at 37° C. Aliquots are removed at time intervals, and combined with an equal volume of MALDI-TOF matrix (α-hydroxycinnamic acid in acetone, 20 mg/ml) and immediately spotted in duplicate onto a stainless-steel MALDI sample plate. MALDI-TOF mass spectrometry is performed on a PE Biosystems Voyager DE instrument at the Molecular Biology Resource Center on campus. The instrument is operated at 25,000 accelerating volts in positive mode with a 150 ns delay. Ions with a mass-to-charge ratio (m/z) are detected in the range of 650-2000 atomic mass units. Data is analyzed by the Voyager Data Explorer module to obtain ion intensity data for mass species of substrates and corresponding products in a given mixture. Relative product formation is calculated as the ratio of signal intensity of the product to the sum of signal intensities of both product and the corresponding substrate. Relative product formed per unit time is obtained from non-linear regression analysis of the data representing the initial 15% formation of product using the model:

$$1-e^{-kT},$$

where k was the relative hydrolytic rate constant and T was time in seconds. Alternatively, relative hydrolytic rates are determined using a fluorogenic cleavage assay (Ermolieff, J. et al., *Biochemistry*, 39: 12450-12456 (2000)). Initial rates from either method are expressed relative to uninhibited controls and the inhibition constant K, was determined by a non-linear fit to a tight-binding model of competitive inhibition (Bieth, J., *Bayer—Symposium V. Proteinase Inhibitors*, pp 463-469, Spinger-Varlag, Berlin (1994)). Results are shown in Table I.

Method Example

Cellular Aβ C$_{50}$ Determinations. The potency of compounds against memapsin 2 catalytic activity is determined in a cellular assay of Aβ production. Compounds that successfully penetrate the cell membrane demonstrate their ability to inhibit memapsin 2 catalytic activity in endosomal compartments, thus blocking the production of Aβ. Chinese hamster ovary cells that over-express human APP695 with the London and Swedish mutations are seeded in multi-well plates at 10% confluency. Compounds are dissolved in DMSO to concentrations near 1 mM, and diluted into culture media to a final concentration near 4 µM (final 0.4% DMSO). Compounds are diluted serially and applied to cells in multi-well plates 48 h after seeding. Incubation is continued in 5% CO$_2$ at 37 degrees C. for 24 h. Aliquots are removed and assayed for Aβ$_{40}$ content using a sandwich ELISA (BioSource International). Amount of Aβ$_{40}$ over the range of concentration of compounds, relative to control incubations, are fit to a 4-parameter IC$_{50}$ model.

Method Example

Tg2576 Transgenic Mouse model. The compounds described herein are injected intraperitoneally into Tg2576 mice (Hsiao, K.; Chapman, P.; Nilsen, S.; Eckman, C.; Harigaya, Y.; Younkin, S.; Yang, F.; Cole, G. Science 1996, 274, 99) and the plasma is sampled immediately prior to and 3 h post-administration. Treatment with the compounds described herein may result in a reduction of Ab40 in plasma, such as at 3 h after a single administration. Doses range from about 0.01 mg/kg to about 100 mg/kg, from about 0.1 mg/kg to about 100 mg/kg, from about 0.1 mg/kg to about 10 mg/kg, from about 1 mg/kg to about 100 mg/kg, or from about 1 mg/kg to about 10 mg/kg. Without being bound by theory, it is believed herein that some of the decrease may likely originate from the reduction of Ab in the brain since Ab in young Tg2576 mice is almost entirely produced in the brain (Kawarabayashi, T.; Younkin, L. H.; Saido, T. C.; Shoji, M.; Ashe, K. H.; Younkin, S. G. J. Neurosci. 2001, 21, 372) and then transferred to the plasma. Also, the plasma Ab has been shown to correlate well with brain Ab in memapsin 2 inhibition using Tg2576 mice (Chang, W. P.; Koelsch, G.; Wong, S.; Downs, D.; Da, H.; Weerasena, V.; Gordon, B.; Devasamudram, T.; Bilcer, G.; Ghosh, A. K.; Tang, J. J. Neurochem. 2004, 89, 1409; Chang, W. P.; Downs, D.; Huang, X. P.; Da, H.; Fung, K.-M.; Tang, J. FASEB J. 2007, 21, 3184). Each of the foregoing publications are incorporated herein by reference.

While certain embodiments of the present invention have been described and/or exemplified above, it is contemplated that considerable variation and modification thereof are possible. Accordingly, it is to be understood that the present invention is not limited to the particular embodiments described and/or exemplified herein.

What is claimed is:
1. A compound of the formula

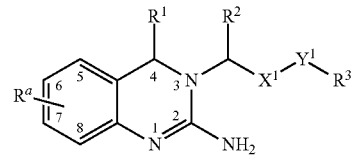

or a pharmaceutically acceptable salt, thereof; wherein
R$^a$ is 6-aryloxy;
R$^1$ is hydrogen;
R$^2$ is cycloalkyl or heterocyclyl, each of which is optionally substituted;
R$^3$ is selected from the group consisting of alkyl, alkenyl, heteroalkyl, cycloalkyl, cycloalkenyl, heterocyclyl, aryl, arylalkyl, heteroaryl, and heteroarylalkyl, each of which is optionally substituted; or R$^3$ and the attached nitrogen form an amino acid or an ester or amide derivative thereof;
X$^1$ is C$_1$-C$_4$ alkylene; and Y$^1$ is N(R$^4$) or OC(O)N(R$^4$);
R$^4$ is hydrogen, or R$^4$ is X$^2$—Z, where X$^2$ is a bond or a C$_1$-C$_4$ alkylene group; and Z is alkyl, alkenyl, heteroalkyl, cycloalkyl, cycloalkenyl, heterocyclyl aryl, or heteroaryl, each of which is optionally substituted.

2. The compound of claim 1 wherein R$^4$ is hydrogen, alkyl, or heteroarylalkyl.

3. The compound of claim 1 wherein R$^3$ is cyclohexyl and R$^2$ is cyclohexyl.

4. The compound of claim 1 wherein R$^2$ is substituted with one or more substituents selected from the group consisting of halogen, hydroxy, alkoxy, haloalkoxy, aryloxy, acyloxy, alkoxycarbonyl, acyl, alkoxycarbonyloxy, alkylsulfonyl, arylsulfonyl, alkylsulfinyl, arylsulfinyl, optionally substituted carbamoyl, optionally substituted amido, optionally substituted carbamoyloxy, amino, optionally substituted ureido, and cyano.

5. The compound of claim 1 wherein $R^3$ is substituted with one or more substituents selected from the group consisting of halogen, hydroxy, alkoxy, haloalkoxy, aryloxy, acyloxy, alkoxycarbonyl, acyl, alkoxycarbonyloxy, alkylsulfonyl, arylsulfonyl, alkylsulfinyl, arylsulfinyl, optionally substituted carbamoyl, optionally substituted amido, optionally substituted carbamoyloxy, amino, optionally substituted ureido, and cyano.

6. The compound of claim 1 wherein $R^2$ is cyclohexyl, tetrahydropyranyl or tetrahydrofuranyl.

7. The compound of claim 1 wherein $R^4$ is heteroarylalkyl, where the heteroaryl is selected from the group consisting of furan, pyrazole, thiazole and oxazole, each of which is optionally substituted and the alkyl is selected from $CH_2$, $(CH_2)_2$, and $CH(CH_3)$.

8. The compound of claim 1 wherein $R^2$ is optionally substituted cyclohexyl.

9. The compound of claim 1 wherein $R^2$ is optionally substituted tetrahydropyranyl or tetrahydrofuranyl.

10. The compound of claim 1 wherein $R^3$ is cycloalkyl or heterocycloalkyl, each of which is substituted with hydroxyl.

11. The compound of claim 1 wherein $R^3$ is optionally substituted cyclohexyl.

12. The compound of claim 1 wherein $R^3$ is optionally substituted phenyl, benzyl or phenethyl.

13. The compound of claim 1 wherein $R^3$ is optionally substituted cyclohexylmethyl or cyclohexylethyl.

14. The compound of claim 1 wherein $R^3$ and the attached nitrogen form an amino acid or an ester or amide derivative thereof.

15. The compound of claim 1 wherein $R^3$ and the attached nitrogen form an ester or amide derivative of an amino acid, where the amino acid is selected from the group consisting of serine, threonine, and alkyl derivatives thereof.

16. The compound of claim 1 wherein $X^1$—$Y^1$ is alkylene-$N(R^4)$.

17. The compound of claim 1 wherein $X^1$—$Y^1$ is methylene-$OC(O)N(R^4)$.

18. A pharmaceutical composition comprising the compound of claim 1 in a therapeutically effective amount for treating Alzheimer's disease, and one or more carriers, diluents, or excipients, or a combination thereof.

19. The compound of claim 1 wherein $R^a$ is 6-phenoxy or 6-pyridyloxy.

20. A method for treating a patient in need of relief from Alzheimer's disease, the method comprising the step of administering to the patient a therapeutically effective amount of a compound of claim 1, or a pharmaceutical composition thereof, where the pharmaceutical composition includes one or more carriers, diluents, or excipients, or a combination thereof.

* * * * *

UNITED STATES PATENT AND TRADEMARK OFFICE
CERTIFICATE OF CORRECTION

PATENT NO. : 8,394,807 B2
APPLICATION NO. : 13/130508
DATED : March 12, 2013
INVENTOR(S) : Arun K. Ghosh It is certified that error appears in the above-identified patent and that said Letters Patent is hereby corrected as shown below:

In the Specifications:

In column 1, line 18, please replace the text "This invention was made with government support under AG 18933 awarded by the National Institutes of Health. The U.S. Government has certain rights in the invention." with the text -- This invention was made with government support under Grant No. AG018933 awarded by The National Institutes of Health. The government has certain rights in the invention. --

Signed and Sealed this
Fourteenth Day of May, 2013

Teresa Stanek Rea
*Acting Director of the United States Patent and Trademark Office*